(12) United States Patent
Stocks et al.

(10) Patent No.: US 6,432,141 B1
(45) Date of Patent: Aug. 13, 2002

(54) JOINT PROSTHESIS ASSEMBLY AND METHOD FOR INSTALLING SAME

(76) Inventors: Gregory W. Stocks, 4919 Valerie, Bellaire, TX (US) 77401; Paul G. Mansour, 2817 Haynes Dr., Midland, TX (US) 79705; Jamie Snelson, 2015 Cedar Bend Dr. Apt. 748, Austin, TX (US) 78758

( * ) Notice: Subject to any disclaimer, the term of this patent is extended or adjusted under 35 U.S.C. 154(b) by 0 days.

(21) Appl. No.: 09/540,446

(22) Filed: Mar. 31, 2000

Related U.S. Application Data

(60) Provisional application No. 60/127,197, filed on Mar. 31, 1999, now abandoned.

(51) Int. Cl.[7] .................................................. A61F 2/34
(52) U.S. Cl. .................. 623/22.13; 623/22.4; 623/23.52
(58) Field of Search ............................ 623/22.13, 22.11, 623/22.15, 22.21, 22.4, 23.11, 23.39, 23.4, 23.52

(56) References Cited

U.S. PATENT DOCUMENTS

| | | | | |
|---|---|---|---|---|
| 3,683,421 A | * | 8/1972 | Martinie | 623/22.13 |
| 3,864,758 A | * | 2/1975 | Yakich | 623/22.13 |
| 4,731,088 A | * | 3/1988 | Collier | 623/22.13 |
| 4,822,368 A | * | 4/1989 | Collier | 623/22.13 |
| 5,514,182 A | * | 5/1996 | Shea | 623/23.4 |
| 5,571,195 A | * | 11/1996 | Johnson | 623/23.44 |
| 5,593,719 A | * | 1/1997 | Dearnaley et al. | 216/83 |
| 5,702,483 A | * | 12/1997 | Kwong | 623/22.4 |
| 5,755,807 A | * | 5/1998 | Anstaett et al. | 623/22.2 |

* cited by examiner

Primary Examiner—David J. Isabella
(74) Attorney, Agent, or Firm—Pandiscio & Pandiscio

(57) ABSTRACT

A joint prosthesis assembly includes a stem for disposition in a canal of a first bone constituting a first portion of the joint, a neck fixed to the stem, a collar fixed on the neck and having a peripheral groove, and an articulating head fixed on the neck. The assembly further includes a cup for disposition in a second bone constituting a second portion of the joint, an insert disposed in the cup to provide an interior lining for the cup, the insert being configured to receive the articulating head for movement therein, and the insert having a peripheral groove therein. A sleeve-shaped membrane is provided with a first O-ring fixed thereto at a first end thereof for disposition in the insert groove, and a second O-ring fixed thereto at a second end thereof for disposition in the collar groove. The membrane is thereby disposed to capture particulate debris generated by the articulating head in the insert. There is further contemplated a method for installing the assembly.

30 Claims, 9 Drawing Sheets

JOINT PROSTHESIS ASSEMBLY AND METHOD FOR INSTALLING SAME

REFERENCE TO PENDING PRIOR PATENT APPLICATION

This application claims the benefit of prior U.S. Provisional Patent Application Serial No. 60/127,197, filed Mar. 31, 1999, now abandoned, by Gregory W. Stocks for ENCAPSULATED HIP REPLACEMENT PROSTHESIS.

FIELD OF THE INVENTION

This invention relates to the field of orthopedic surgery in general, and more specifically to a joint prosthesis assembly and method for installing same.

BACKGROUND OF THE INVENTION

A natural hip joint is a ball and socket joint in which a hemispherical head moves freely within a concave socket.

Artificial hip joints are an approximation of natural hip joints. More particularly, artificial hip joints consist of a metal (or metal alloy) head which articulates inside a metal (or metal alloy) cup. Often the metal socket is lined with very dense plastic, typically Ultra High Molecular Weight Polyethylene (UHMWPE), so as to reduce friction in the artificial bearing.

In 1994, 165,000 total hip replacements (THR's) were performed in the United States. Due to the success of the THR operation, the improved quality of life it provides, and the increasing elderly population, this number is expected to increase in the future.

The expected life of an artificial hip is less than 10 years in active adults and about 10–20+ years in less active adults. When the artificial hip wears out, it must be replaced with a new artificial hip. This procedure is typically referred to as a "revision". In 1994, THR revision surgery accounted for approximately 20% of all THR surgery, and is expected to increase inasmuch as many patients are receiving THR's at an earlier age. According to The National Center For Health Statistics, the annual number of total hip revisions will increase to 157,000 by the year 2010 and 219,000 by the year 2030.

THR revision surgery is typically more complex, time-consuming and complication-prone than standard THR surgery.

Accordingly, it is desirable to find a way to extend the life of the artificial hip.

According to the National Institutes of Health, "the principle cause of prosthesis failure appears to be the generation of particles, which, in turn, cause inflammation and bone resorption around the prosthesis (osteolysis)" (NIH Consensus Statement: Total Hip Replacement. 1994; 12:1–31). The problem of osteolysis in THR involves three aspects: (a) the creation of debris particles within the artificial joints; (b) the migration of the debris particles to the bone around the prosthesis; and (c) a cellular reaction to the debris particles.

Extensive research has been published regarding the aforementioned first and third aspects of the problem.

More particularly, some current work is aimed at reducing the production of wear particles at the bearing surface of the artificial joint by using new metal-on-metal bearing designs, or modifying existing metal-polyethylene hips; however, it is unlikely that these modifications will eliminate wear particles completely, some of which have been found in the liver, spleen, and lymph nodes, and have been implicated as a cause of cancer.

Research aimed at reducing osteolysis by better understanding and controlling the biological cellular response, the third aspect described above, is widespread. Currently, a clinically useful approach has not been elucidated, although anti-inflammatory medications and anti-osteoclast medications show promise. Many investigators, however, have reservations about treating a localized problem with a systemic agent.

The present invention addresses the problem of osteolysis by focusing on the second aspect identified above, i.e., the migration of the debris particles to the bone around the prosthesis. More particularly, the present invention provides an improved "Sealed-Bearing" total hip replacement (SB-THR) which incorporates the use of a limiting membrane that encapsulates the bearing and prevents debris particles from migrating from the prosthesis to the surrounding bone. The SB-THR could potentially eliminate osteolysis in the primary THR, thereby sparing thousands of patients from the ordeal of revision surgery and effecting significant savings in health care costs to society.

In addition, the SB-THR has the additional advantage that it can prevent so-called "third bodies" from entering the space between the femoral head and the pelvic socket, where they can accelerate wear on the head and the socket. Such "third bodies" typically comprise small pieces of bone which are created during the milling process when the femoral canal is prepared or the socket seat is prepared; and/or small pieces of the prosthesis which may flake off the outer surface of the prosthesis, e.g., hydroxyapetite or porous metal for encouraging bone ingrowth.

There has been some prior work in the area of the sealed-bearing concept. See, for example, U.S. Pat. Nos. 4,731,088 (Collier), U.S. Pat. No. 5,514,182 (Shea), and U.S. Pat. No. 5,755,807 (Anstaett et al.).

Accepting that the sealed bearing membrane is advantageous in eliminating or discouraging migration of debris particles, it becomes critical that the sealing membrane itself not present a problem, as by disconnection from a member of the joint.

A further complication lies in the fact that a sealing membrane in the hip joint flexes, when a leg is moved, not only in a bending direction, but also in a twisting or rotating direction, in which the sleeve-like membrane twists around its central axis.

There is, therefore, a need for a membrane adapted to encapsulate a bodily joint, such as a hip joint, so as to prevent migration of debris particles. There is further a need for securely attaching the membrane to the members of the joint. A related further need exists for effecting long term attachment of the membrane to the members of the joint, such that upon gradual elimination of holding power of the initial attachment means, other attachment means grow stronger and increase the holding security of the membrane. A still further need exists for compensating for the bend-and-twist movement of the membrane in hip assemblies, such that undue strain from repetitive movement does not weaken the structure of the membrane. And a still further need is to provide an improved total joint replacement assembly which may be used in joints other than the hip, e.g., the knee, the shoulder, the elbow, etc.

OBJECTS OF THE INVENTION

It is, therefore, an object of the invention to provide a sealed-bearing type of total hip replacement assembly and/or other total joint replacement assembly.

A further object of the invention is to provide such an assembly which includes an encapsulating membrane which captures and prevents migration of debris particles.

A further object of the invention is to provide such a membrane having thereon means for accurately and securely attaching the membrane to supporting structures at either end thereof.

A still further object of the invention is to provide such a membrane as permits localized ingrowth of tissue to further secure the membrane to the supporting structures.

A still further object of the invention is to provide such a membrane configured to reduce stress fatigue of the membrane resulting from long term use of the membrane.

A still further object of the invention is to provide a method for installing such an assembly.

SUMMARY OF THE INVENTION

With the above and other objects in view, as will hereinafter appear, a feature of the present invention is the provision of a joint prosthesis assembly, the assembly comprising a stem for disposition in a canal of a first bone constituting a first portion of the joint, a neck fixed to the stem, a collar fixed on the neck, the collar having a peripheral annular groove therein, and an articulating head fixed on the neck, the assembly further comprises a cup for disposition in a second bone constituting a second portion of the joint, and an insert disposed in the cup to provide an interior lining for the cup, the insert being adapted to receive the articulating head for movement therein, the insert having a peripheral annular groove therein. A sleeve-shaped membrane is provided with a first O-ring fixed thereto at a first end thereof for disposition in the insert groove, and a second C-ring fixed thereto at a second end thereof for disposition in the collar groove. The membrane is thereby disposed to capture particulate debris generated by the articulating head in the insert.

In accordance with a further feature of the invention, there is provided a joint prosthesis assembly comprising a stem for disposition in a canal of a first bone constituting a first portion of the joint, a neck fixed to the stem, a collar fixed on the neck, and an articulating head fixed on the neck. The assembly further comprises a cup for disposition in a second bone constituting a second portion of the joint, and an insert disposed in the cup to provide an interior lining for the cup, the insert being adapted to receive the articulating head for movement therein. A sleeve-shaped membrane is provided with a first connector structure fixed thereto at a first end thereof for connection to the insert, and a second connector structure fixed thereto at a second end thereof for connection to the collar. The membrane is thereby disposed to capture particulate debris generated by the articulating head in the insert. A first end portion of the membrane proximate the first end of the membrane and a second end portion of the membrane proximate the second end of the membrane have apertures therein permitting ingrowth of tissue to further secure the membrane in an operative position, and a middle portion of the membrane is devoid of apertures therein permitting ingrowth of tissue.

In accordance with a still further feature of the invention, there is provided a joint prosthesis assembly comprising a stem for disposition in a canal of a first bone constituting a first portion of the joint, a neck fixed to the stem, a collar fixed on the neck, and an articulating head fixed on the neck. The assembly further comprises a cup for disposition in a second bone constituting a second portion of the joint, and an insert disposed in the cup to provide an interior lining for the cup, the insert being adapted to receive the articulating head for movement therein. The assembly further includes a sleeve-shaped membrane having a first connector structure fixed thereto at a first end thereof for connection to the insert, and a second connector structure fixed thereto at a second end thereof for connection to the collar, the membrane being thereby disposed to capture particulate debris generated by the articulating head in the insert. The first and second ends are circularly displaced from each other around a central axis therethrough by an angle of about 35°–55°.

In accordance with still another feature of the invention, there is provided a joint prosthesis assembly comprising a stem for disposition in a canal of a first bone constituting a first portion of the joint, a neck fixed to the stem, a collar fixed on the neck, and an articulating head fixed on the neck. The assembly further includes a cup for disposition in a second bone constituting a second portion of the joint, and an insert disposed in the cup to provide an interior lining for the cup, the insert being adapted to receive the articulating head for movement therein. The assembly further comprises a sleeve-shaped membrane having a first connector structure fixed thereto at a first end thereof for connection to the insert, and a second connector structure fixed thereto at a second end thereof for connection to the collar. The membrane is thereby disposed to capture particulate debris generated by the articulating head in the insert. A middle portion of the membrane is formed so as to be pre-stressed in a circular direction around a central axis therethrough, by an angle of about 35°–55°.

In accordance with a still further feature of the invention, there is provided a method for installing a joint prosthesis assembly. The method comprises the steps of providing a joint prosthesis assembly comprising a stem for disposition in a canal of a first bone constituting a first portion of the joint, a neck fixed to the stem, a collar fixed on the neck, the collar having a peripheral annular groove therein, an articulating head fixed on the neck, a cup for disposition in a second bone constituting a second portion of the joint, an insert disposed in the cup to provide an interior lining for the cup, the insert being adapted to receive the articulating head for movement therein, the insert having a peripheral annular groove therein, and a sleeve-shaped membrane having a first O-ring fixed thereto at a first end thereof for disposition in the insert groove, and a second O-ring fixed thereto at a second end thereof for disposition in the collar groove. The method includes the further steps of mounting a first sub-assembly of the stem, neck, collar and articulating head on the first bone, mounting a second sub-assembly of the cup and insert on the second bone, mounting the membrane around the articulating head, fitting the articulating head in the insert, placing the first O-ring in the insert groove to fix the membrane first end to the insert, and placing the second O-ring in the collar groove to fix the membrane second end to the collar. The membrane is thereby disposed to capture particulate debris generated by the articulating head in the insert.

The above and other features of the invention, including various novel details of construction and combinations of parts, will now be more particularly described with reference to the accompanying drawings and pointed out in the claims. It will be understood that the particular assembly and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

The above and other objects and features of the present invention will be more fully disclosed in the following detailed description of the preferred embodiments of the invention, which is to be considered together with the accompanying drawings wherein like numbers refer to like parts, and further wherein.

DETAILED DESCRIPTION OF THE PREFERRED EMBODIMENT

Figure 1:
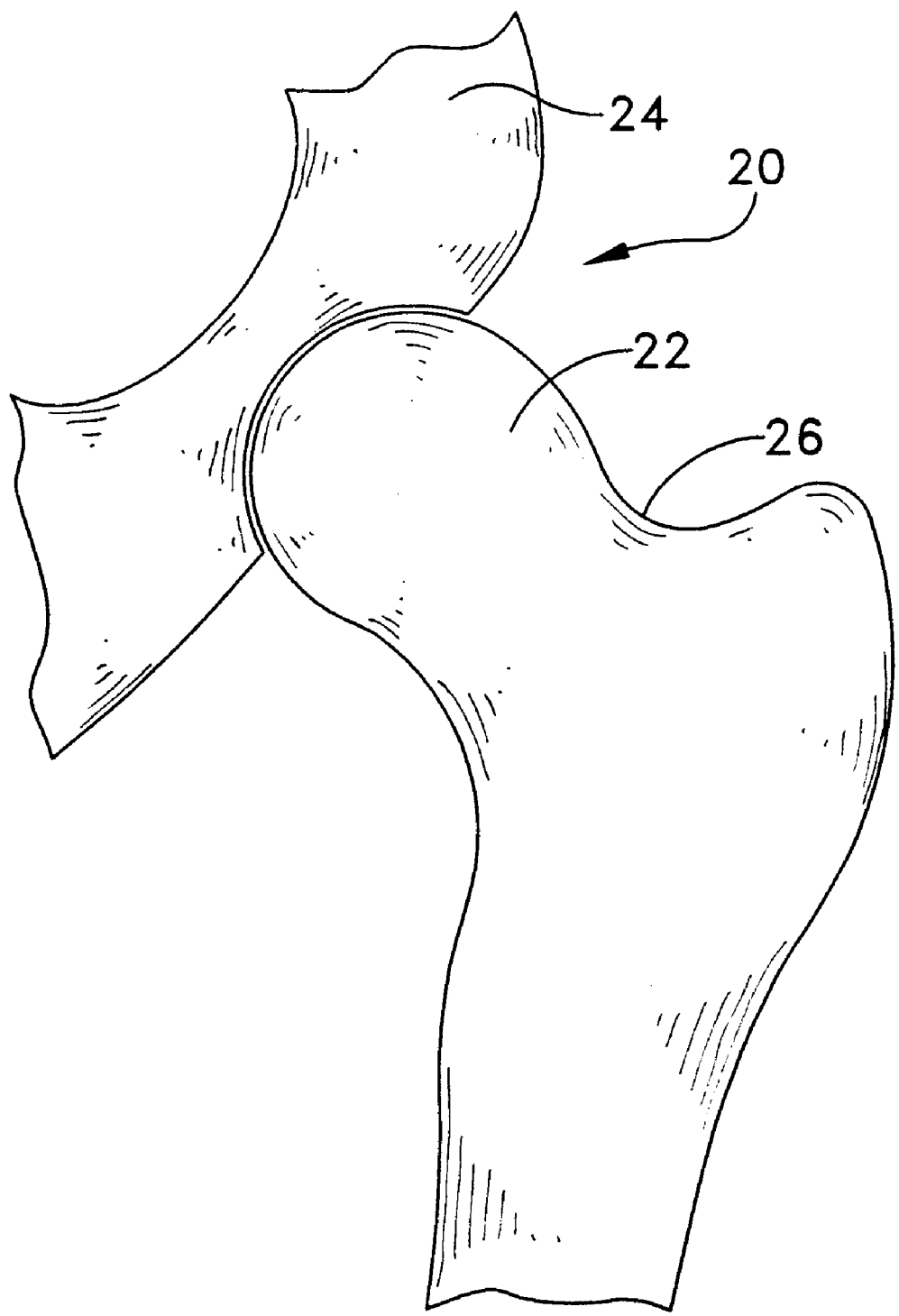
FIG. 1 is a diagrammatic illustration of a natural hip joint.

Referring to FIG. 1, it will be seen that a natural hip joint 20 comprises a femoral head portion 22, which is generally hemispherical in shape, and which articulates freely in an acetabulum 24, forming a natural bearing. A natural semi-permeable sack or bursa (not shown), generally referred to as the capsule of the hip joint, surrounds the bearing, enclosing synovial fluid, which serves to lubricate the bearing. The femoral head portion 22 extends to a femoral neck portion 26, which is sufficiently narrow to allow full range of motion.

Figure 2:
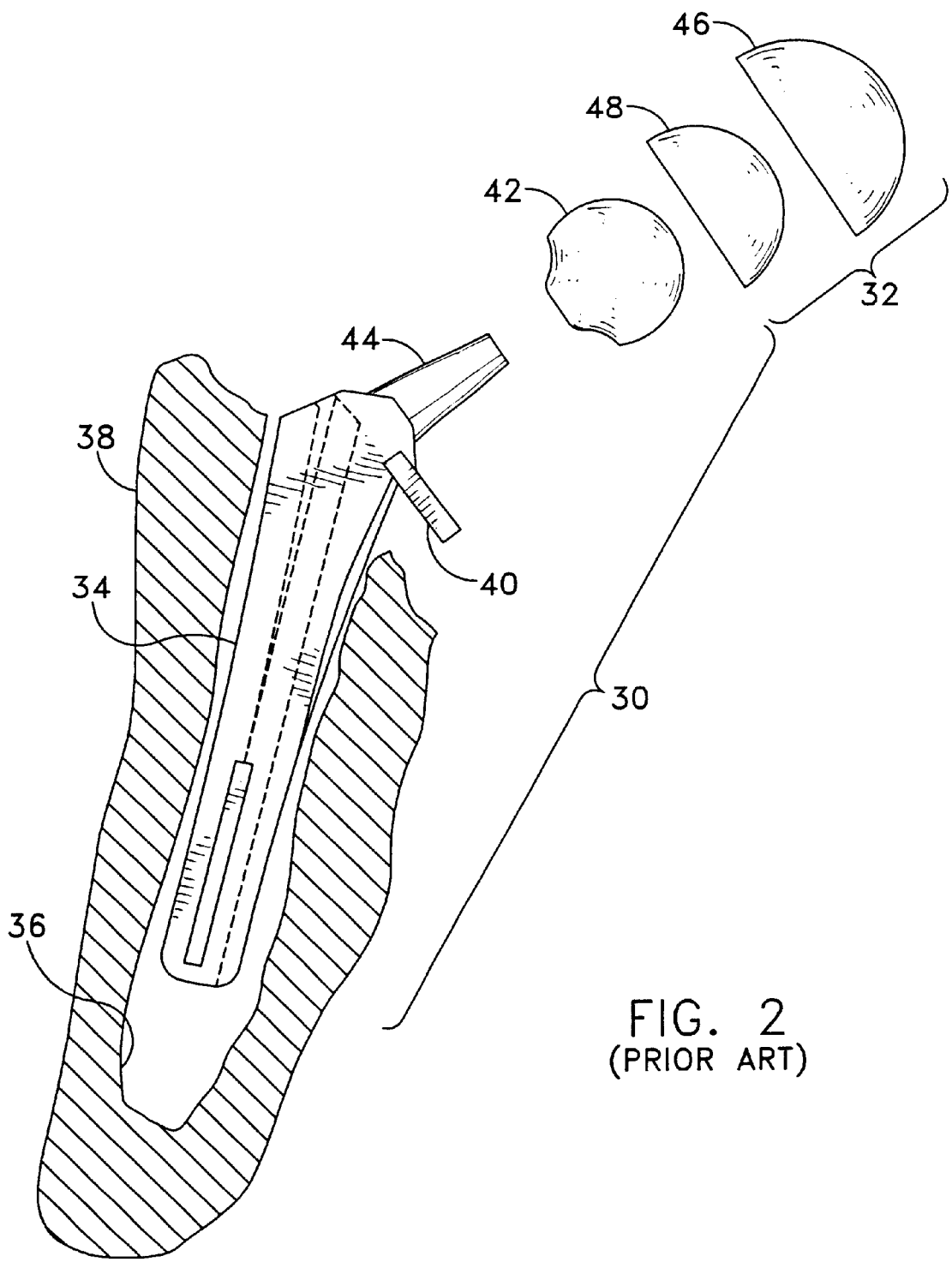
FIG. 2 is a diagrammatic exploded view, partly in section, of a prior art total hip replacement assembly.

A prior art artificial hip (FIG. 2) approximates the major components of the natural joint 20. The artificial hip is typically made of metal or metal alloy. Traditionally, a hip prosthesis consists of a femoral sub-assembly 30 and an acetabular sub-assembly 32. The artificial femoral subassembly 30 includes a stem 34, which is inserted into a canal 36 in the patient's femur 38 for support and load distribution. During hip replacement surgery, an incision is made and the patient's hip is dislocated, revealing the patient's femoral head 22 (FIG. 1) and acetabulum 24 (FIG. 1). The patient's femoral head 22 (FIG. 1) is removed and the canal 36 (FIG. 2) is drilled into the patient's femur 38. The artificial stem 34 is fitted into the canal 36, often using bone cement for anchorage. When bone cement is not used, part of the stem 34 may be textured or covered with Titanium mesh (or similar network) to promote bone in-growth. Often, there is a lip 40 for the distribution of load across the femur 38. An end of the femoral sub-assembly 30 is an articulating head 42 which may be permanently attached or press fit onto a femoral neck 44, in which case the femoral neck 44 is generally in the shape of a Morris taper to ensure a tight, slip-resistant fit.

Figure 3:
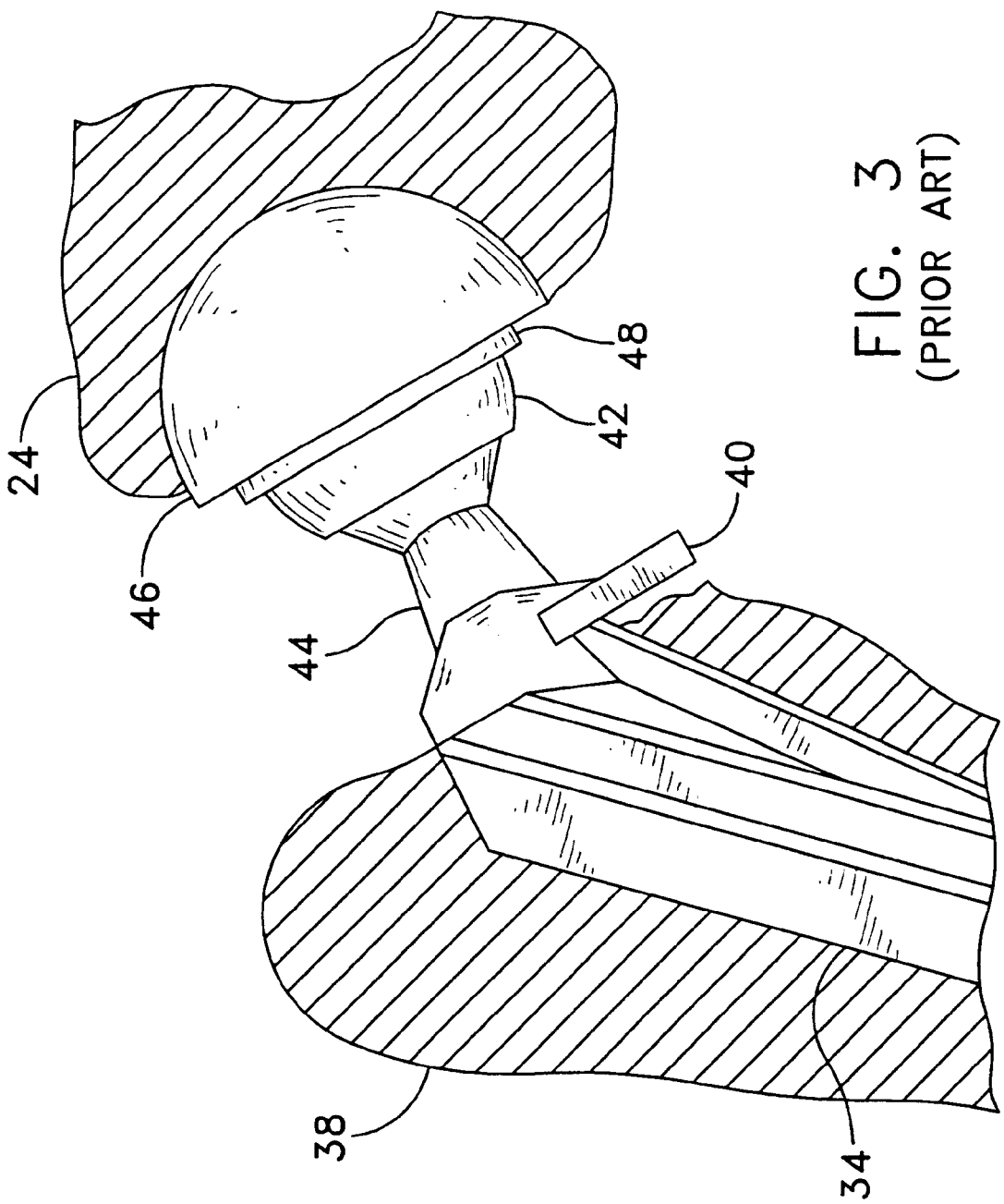
FIG. 3 is a diagrammatic, partly sectional, view of the prior art assembly of FIG. 2 installed.

The acetabular sub-assembly 32 comprises a cup 46 in which the articulating head 42 articulates. The acetabular cup 46 may be screwed and/or glued into the patient's acetabulum 24 (FIG. 3). Often, the outer surface of the cup 46 is covered in Titanium mesh, or similar network, to promote bone in-growth. An insert 48, typically of plastic material, is usually placed between the articulating head 42 and the acetabular cup 46 to reduce load and friction in the bearing. The insert 48 may be made of high density plastic such as Ultra High Molecular Weight Polyethylene (UHMWPE). Once installed, the patient's hip is relocated and the incision is closed.

Figure 4:
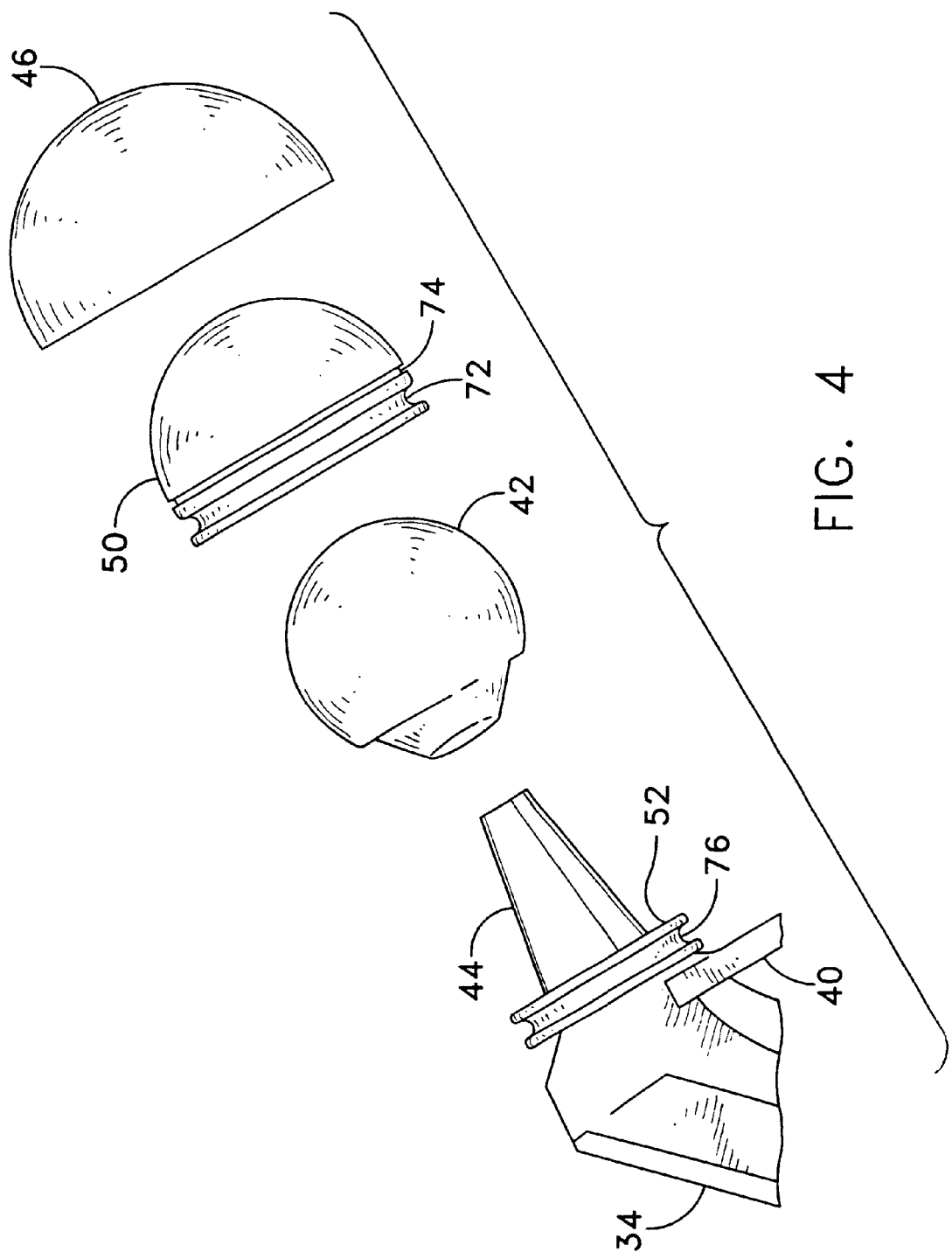
FIG. 4 is an elevational exploded view of one form of total hip replacement assembly, less an encapsulating membrane portion, illustrative of an embodiment of the invention.
Figure 5:
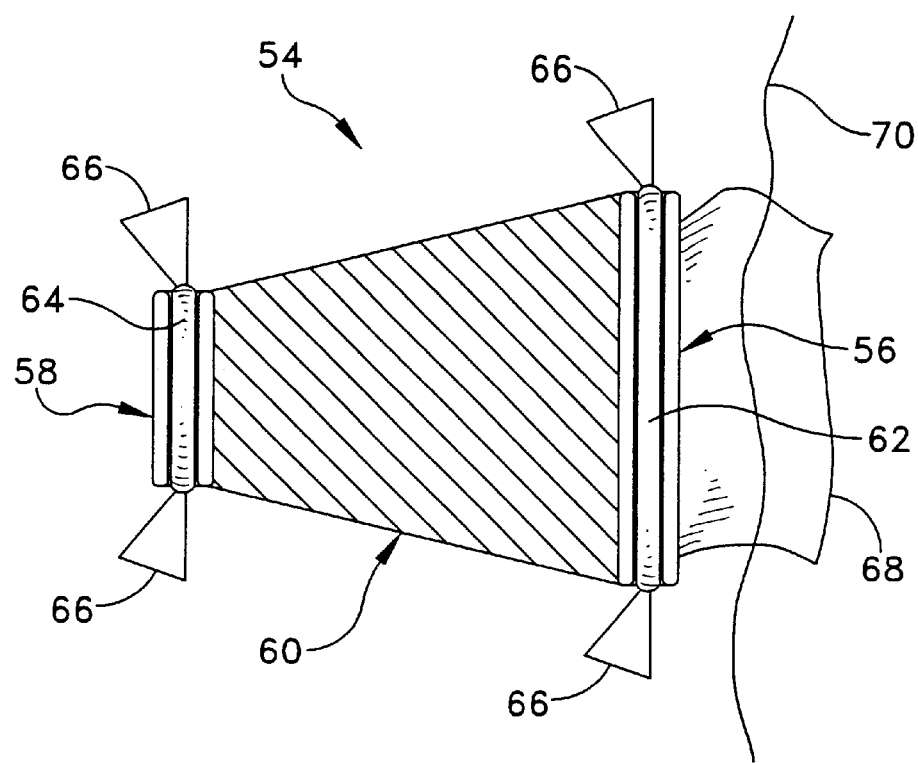
FIG. 5 is a diagrammatic elevational illustration of an encapsulating membrane portion for use with the assembly of FIG. 4.

The assembly of the present invention is adapted to encapsulate the bearing of the prosthesis, to prevent migration of wear particles that are generated by the articulation of the femoral head portion 42 and the acetabular cup 46, or insert 48. In addition, the assembly of the present invention can prevent so-called "third bodies" from migrating into the bearing area of the prosthesis. Improvements which are made to the current artificial hip prosthesis, and described herein, include an increased offset dual-groove UHMWPE insert 50 (FIG. 4), a femoral collar 52, and a sleeve-shaped encapsulating membrane 54 (FIG. 5).

The encapsulating membrane 54 is made of biocompatible material, such as Cytoplast SB™, and can easily be extruded into any desired thickness. The sleeve shape of the membrane 54 preferably is generally frusto-conical, having a larger circular acetabular end 56, a smaller circular femoral end 58, and a middle portion 60 extending therebetween. Both ends 56, 58 of the membrane 54 have a connector structure, preferably an attached O-ring 62, 64, respectively, made of the same or similar material as the membrane 54 for fastening the membrane 54 to the insert 50 and femoral collar 52. Each O-ring 62, 64 is provided with tabs 66, preferably set equidistant from each other along its circumference, to provide a surgeon with a place to hold for pulling the membrane 54 into place and adjusting its location. The tabs 66 may be made of the same material as the membrane 54 and may be textured to provide additional "growth points" for the natural bursa to attach when it regenerates after surgery. The end 56 of the membrane 54 with the larger diameter is, preferably, provided with a flexible flap 68 that extends along at least a portion of the membrane's circumference. A suture 70 is contained in the flap 68 to aid in the installation of the membrane 54, as will be discussed below.

Figure 6:
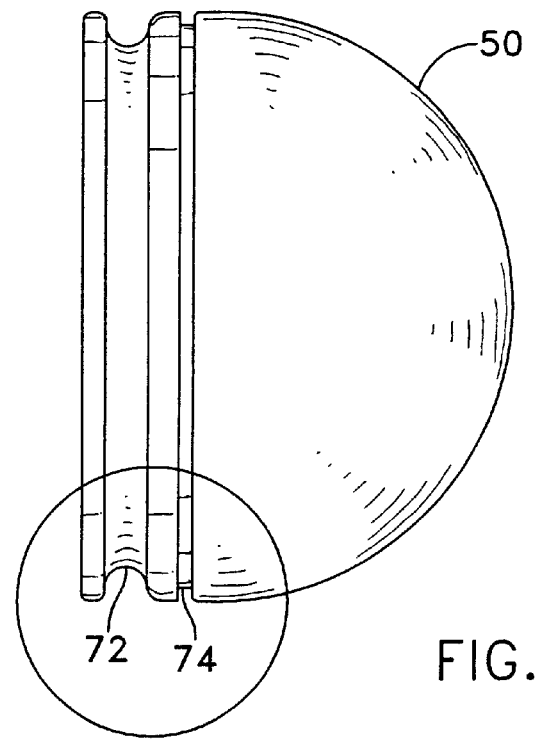
FIG. 6 is a side elevational view of an insert portion of the assembly of FIG. 4.
Figure 7:
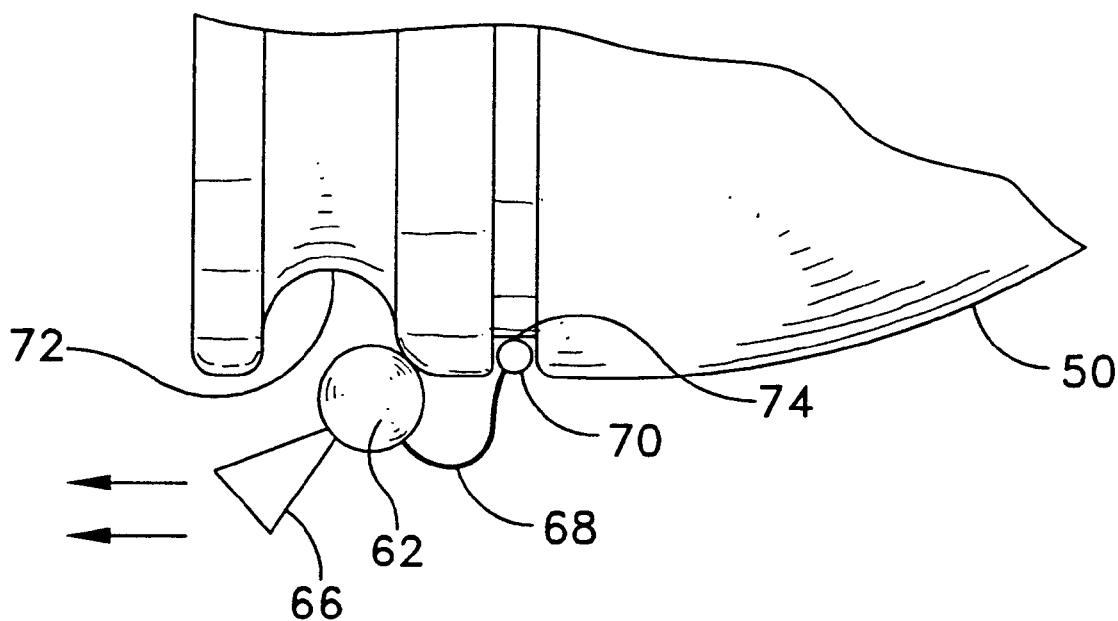
FIG. 7 is an enlarged illustration of a boxed portion of the insert portion of FIG. 6.

Referring to FIGS. 6 and 7, it will be seen that the insert 50 is provided with two grooves 72, 74. The groove 72 is located close to the open end of the insert 50 and is used to seat and secure the O-ring 62 on the larger end 56 of the membrane 54. The groove 74 is disposed approximately 1.5 mm behind groove 72 and is used to seat the suture 70, which acts as a guide to direct the placement of the O-ring.

During installation, visibility in the area of the membrane end 56 can be limited. To attach the end 56 of the membrane to the insert 50, the surgeon grasps both ends of the suture 70 and fits the suture 70 in the groove 74, substantially by "feel" in some cases. The suture 70 is secured, as by tying, in the groove 74. The tabs 66 are then pulled until the O-ring 62 pops into place in the groove 72 (FIG. 7). In effect, suture 70 acts as something of a pursestring to secure (sometime substantially by feel alone) flexible flap 68 to groove 74 in insert 50; thereafter, tabs 66 can be used to manipulate O-ring 62 into groove 72 in insert 50.

The femoral sub-assembly 30 is provided with the elliptical femoral collar 52 (FIGS. 4 and 8) around the femoral neck portion 44, with a groove 76 formed along its perimeter. The O-ring 64 from the smaller end 58 of the membrane 54 is seated in the groove 76.

Figure 8:
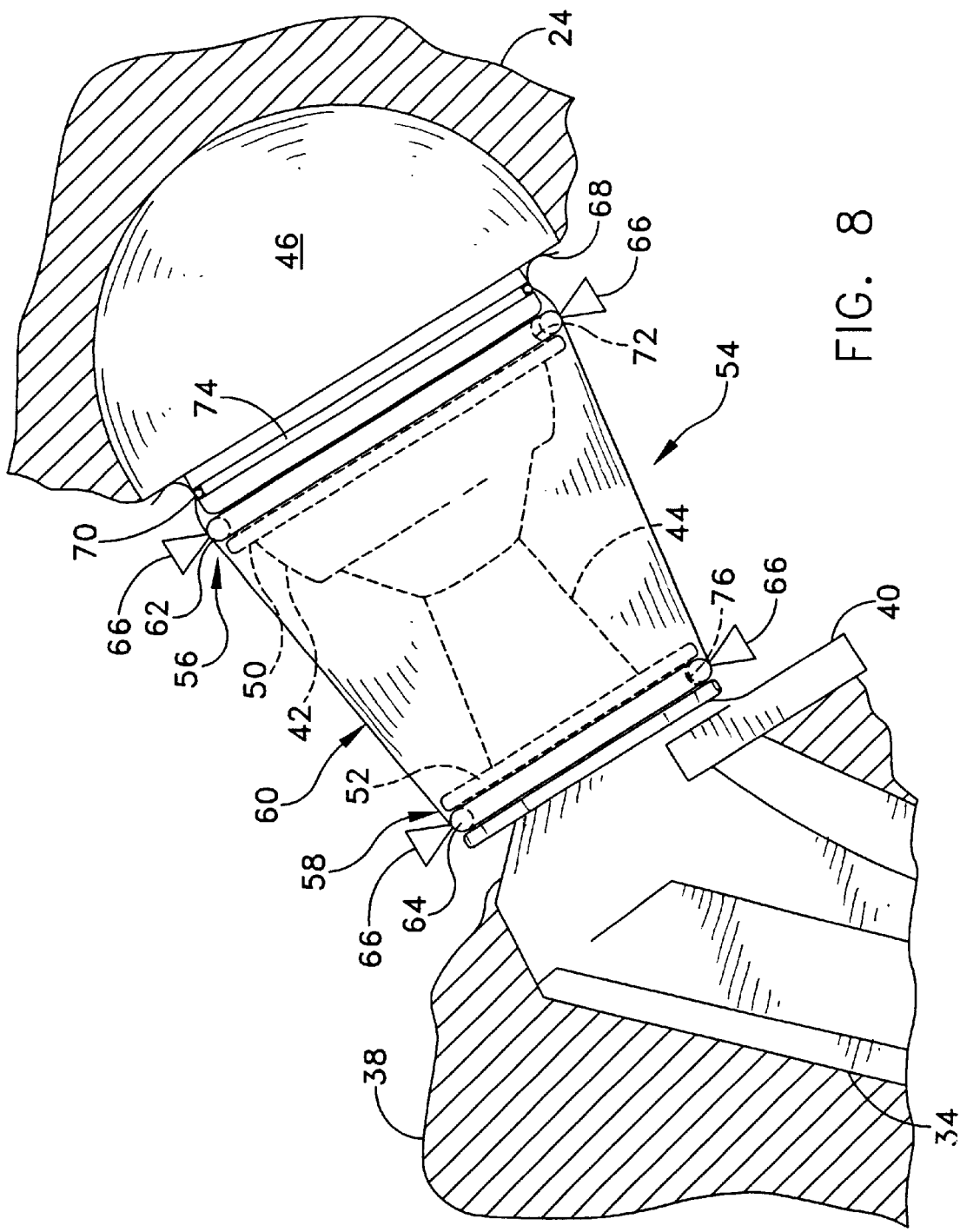
FIG. 8 is a diagrammatic, partly sectional, view of the assembly of FIGS. 4 and 5 combined and in operative position.
Figure 9:
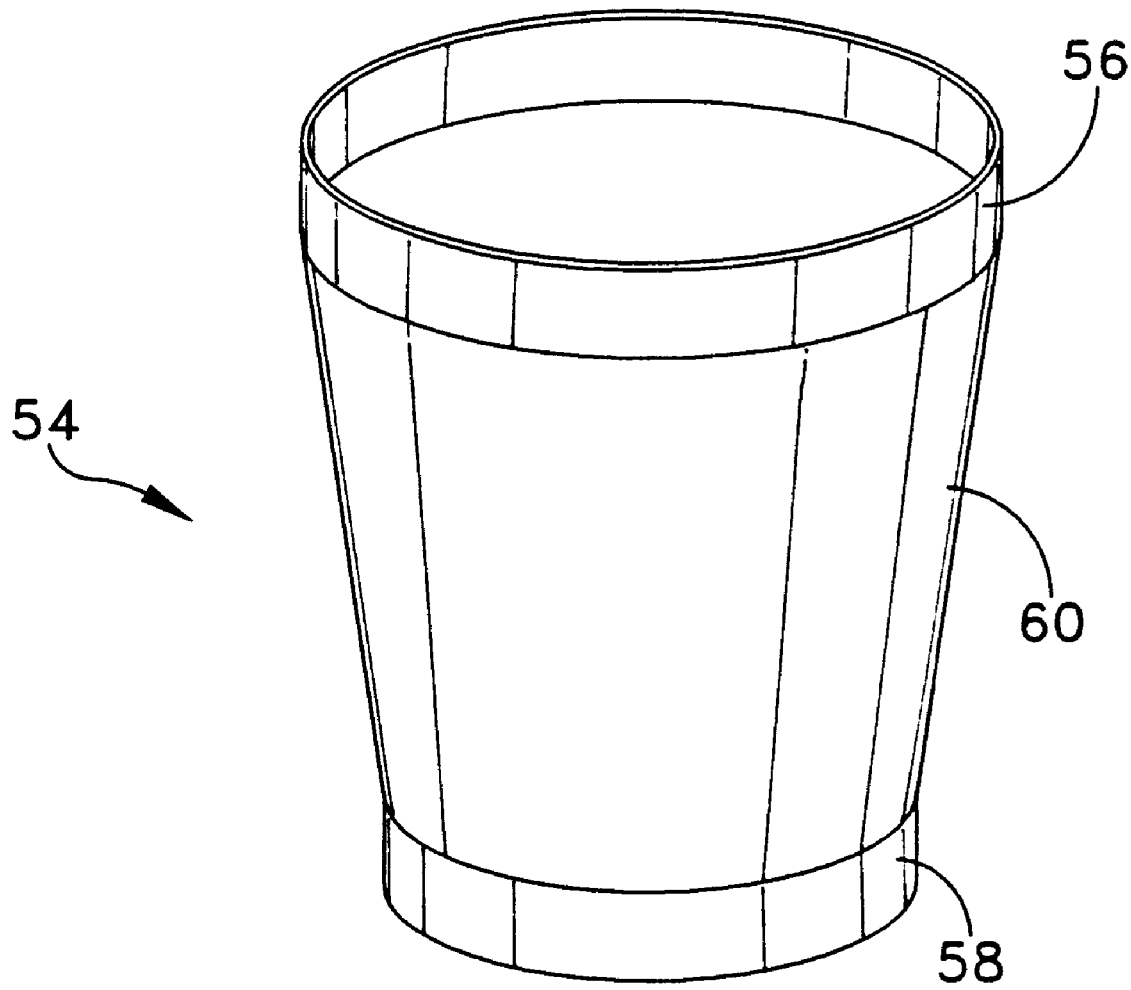
FIG. 9 is a diagrammatic perspective view of the encapsulating membrane portion wherein, for clarity of illustration, selected structures have been omitted from view.

As shown in FIGS. 5, 8 and 9, the encapsulating membrane 54 includes the first (acetabular) end portion 56, the middle portion 60, and the second (femoral) end portion 58. The end portions 56, 58 are the portions which are anchored to the joint members, while the middle portion 60 is not directly anchored to joint members or tissue. The ends 56, 58 are fabricated so as to be porous, or otherwise are provided with apertures or recesses or texture or surface treatment or the like, all of which constructions are intended to be encompassed by the general term "apertures", so as to encourage tissue ingrowth. The middle portion 60 is fabricated so as to discourage tissue ingrowth, as by being made substantially non-porous, or otherwise without apertures or recesses or texture or surface treatment or the like of sufficient size to permit ingrowths, all of which constructions are intended to be encompassed by the general term "devoid of apertures".

Thus, if after a period of years the O-rings 62, 64 suffer from fatigue and their holding power is diminished, the ingrowth of tissue through the membrane end portions 56, 58 serves to maintain the membrane securely affixed at either end.

By way of example but not limitation, encapsulating membrane 54 may be formed out of PTFE, with end portions 56, 58 being formed out of expanded PTFE so as to encourage tissue ingrowth, and with middle portion 60 being formed out of non-expanded PTFE so as to prevent tissue ingrowth.

If desired, membrane 54 may include an antibiotic to minimize the risk of infection associated with hip replacement surgery. The antibiotic may be applied to the surface of the membrane as a coating, or it may be impregnated into the material of the membrane.

Figure 10:
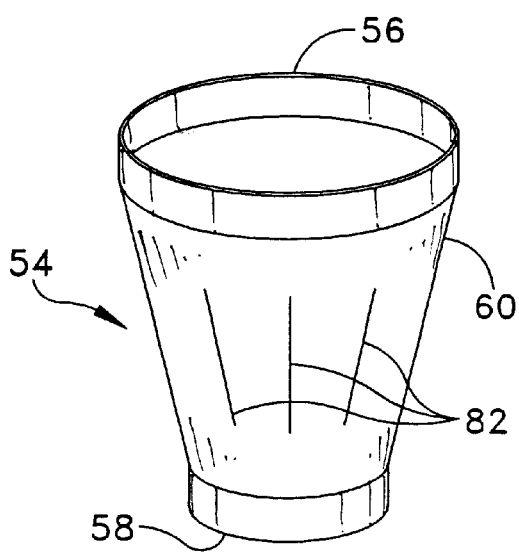
FIGS. 10 and 11 are diagrammatic views of an encapsulating membrane, illustrating an operational feature of prior art membranes.
Figure 11:
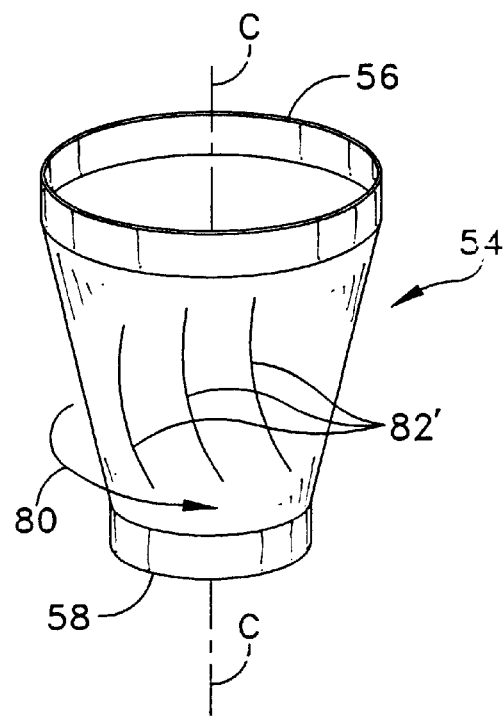

In FIGS. 10 and 11, there is illustrated the known fact that in hip joints, when a proximate leg is flexed, the membrane 54 covering the joint twists, as for example, in the direction indicated by arrow 80 in FIG. 11. It is known that the twist around the central axis c—c is about 45°±10°. Thus, the membrane 54 is continually moved from a substantially relaxed position, as indicated in FIG. 10 wherein hypothetical straight lines 82 illustrate the relaxed, unstressed state of the membrane middle portion 60, to a stressed condition, indicated in FIG. 11 wherein hypothetical curved lines 82' illustrate the stressed state of the membrane middle portion 60. It will be apparent that continually stressing and relaxing the membrane 54 in this manner eventually introduces fatigue into the membrane structure, which may lead to the rupture or tearing of the membrane and the escape of debris.

Figure 12:
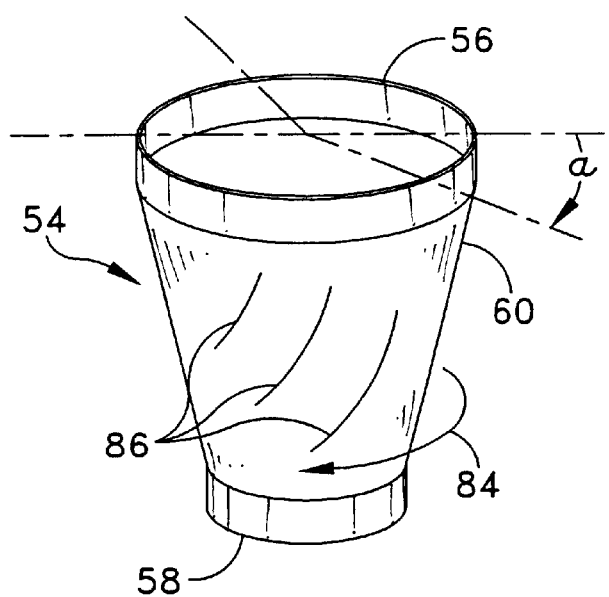
FIGS. 12 and 13 are similar to FIGS. 10 and 11, but illustrative of a feature of the inventive encapsulating membrane.
Figure 13:
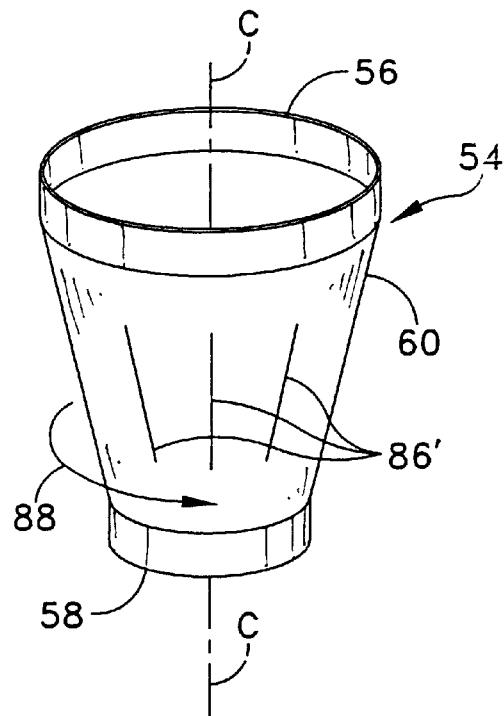

It has been found to be beneficial to provide the membrane with a pre-set twist of about 45° in the direction opposite to arrow 80, that is, in the direction of arrow 84 in FIG. 12. The pre-setting of the twist may be built into the membrane middle portion 60, as by alignment of fibers in the material of the middle portion, or may be introduced by the surgeon at the time of the THR operation. In the latter case, the surgeon manually shifts one end of the membrane through angle a, preferably an estimated 45°, before securing that end in place. Thereafter, upon flexing of the proximate leg, the "stressed" state, indicated by hypothetical lines 86 in FIG. 12, is relieved, indicated by hypothetical lines 86' in FIG. 13, by movement of the middle portion 60 of the membrane 54 in the direction of arrow 88 around the central axis c—c.

Installation of the above-described assembly requires the steps of mounting the femoral sub-assembly 30, including the stem 34, neck 44, collar 52 and articulating head 42 on the first bone 38, mounting the acetabular sub-assembly 32, including the cup 46 and insert 50 on the second bone 24, mounting the membrane 54 around the articulating head 42, fitting the articulating head 42 in the insert 50, placing the first O-ring 62 in the insert groove 72 to fix the membrane first end 56 to insert 50, and placing the second O-ring 64 in the collar groove 76 to fix the membrane second end 58 to the collar 52, the membrane being thereby disposed to capture particulate debris generated by the articulating head 42 in the insert 50. In addition, membrane 54 can also prevent so-called "third bodies" from migrating into the bearing area of the prosthesis.

Alternatively, if desired, the membrane's second O-ring 64 can be seated in collar groove 76 before its first O-ring 62 is seated in insert groove 72.

In cases in which the aforesaid twist is desired, and is not formed or pre-set in the membrane 54, the above-described method is modified to include the further step of twisting the membrane 54 circularly about its central axis c—c, about 35°–55°, before securing the last of the first O-ring 62 to insert 50 and the second O-ring 64 to the collar 52 with the membrane 54 in a twisted state.

The method described herein, and particularly the step of placing the first O-ring 62 in the insert groove 72 preferably further includes the steps of placing the strand of suture 70 in the insert suture groove 74, tightening and tying the strand of suture 70 in the insert suture groove 74, and manipulating the tabs 66 to pull the first O-ring 62 toward the insert peripheral annular groove 72 until the first O-ring 62 snaps into the insert peripheral annular groove 72, to fix the membrane first end 56 to the insert 50.

There is thus provided an improved sealed-bearing total hip prosthesis including an encapsulating membrane having (1) improved means for securely mounting at the site, (2) means for further securing at the site over time, and (3) means for relieving stress fatigue therein. In addition, there is provided an improved total joint replacement assembly which may be used in joints other than the hip, e.g., the knee, the shoulder, the elbow, etc.

There is further provided a method for installing the above-described prosthesis assembly.

It is to be understood that the present invention is by no means limited to the particular construction and method steps herein disclosed and/or shown in the drawings, but also comprises any modifications or equivalents within the scope of the claims.

What is claimed is:

1. A joint prosthesis assembly comprising:
    a stem for disposition in a canal of a first bone constituting a first portion of the joint;
    a neck fixed to said stem;
    a collar fixed on said neck, said collar having a peripheral annular groove therein;
    an articulating head fixed on said neck;
    a cup for disposition in a second bone constituting a second portion of the joint;
    an insert disposed in said cup to provide an interior lining for said cup, said insert being adapted to receive said articulating head for movement therein, said insert having a peripheral annular groove therein; and
    a sleeve-shaped membrane having a first O-ring fixed thereto at a first end thereof for disposition in the insert groove, and a second O-ring fixed thereto at a second end thereof for disposition in the collar groove, said membrane being thereby disposed to capture particulate debris generated by said articulating head in said insert.

2. A joint prosthesis assembly in accordance with claim 1 wherein said membrane includes a first end portion at the first end thereof, a second end portion at the second end thereof, and a middle portion therebetween, the end portions having apertures therein permitting ingrowth of tissue to anchor the ends at an operative site, and the middle portion being devoid of apertures permitting ingrowth of tissue.

3. A joint prosthesis assembly in accordance with claim 1 wherein the first and second ends are circularly displaced from each other around a central axis therethrough by an angle of about 35°–55°.

4. A joint prosthesis assembly in accordance with claim 1 wherein the membrane further includes a middle portion between the first and second ends thereof, the middle portion being formed so as to be pre-stressed in a circular direction, around a central axis thereof, at an angle of about 35°–55°.

5. A joint prosthesis assembly in accordance with claim 1 wherein said insert is further provided with an annular suture groove proximate said insert peripheral annular groove, said membrane is provided with a flexible flap extending from the membrane first end and having a strand of suture fixed thereto, and the insert suture groove is adapted to receive the strand of suture, to place the first O-ring in a position proximate the insert peripheral annular groove.

6. A joint prosthesis assembly in accordance with claim 1 and further comprising tabs fixed to each of the O-rings for manual manipulating of the O-rings.

7. A joint prosthesis assembly in accordance with claim 5 and further comprising tabs fixed to the first O-ring to facilitate pulling the first O-ring from the position proximate the insert peripheral annular groove to a second position at which the first O-ring snaps into the insert peripheral annular groove.

8. A joint prosthesis assembly in accordance with claim 1, wherein said membrane is generally frusto-conically shaped.

9. A joint prosthesis assembly in accordance with claim 8 wherein the joint comprises a hip joint, and the membrane is provided with a larger acetabular end and a smaller femoral end.

10. A joint prosthesis assembly comprising:
   a stem for disposition in a canal of a first bone constituting a first portion of the joint;
   a neck fixed to said stem;
   a collar fixed on said neck;
   an articulating head fixed on said neck;
   a cup for disposition in a second bone constituting a second portion of the joint;
   an insert disposed in said cup to provide an interior lining for said cup, said insert being adapted to receive said articulating head for movement therein;
   a sleeve-shaped membrane having a first connector structure fixed thereto at a first end thereof for connection to said insert, and a second connector structure fixed thereto at a second end thereof for connection to said collar, said membrane being thereby disposed to capture particulate debris generated by said articulating head in said insert;
   a first end portion of said membrane proximate the first end of said membrane and a second end portion of said membrane proximate the second end of said membrane having apertures therein permitting ingrowth of tissue to further secure said membrane in an operative position; and
   a middle portion of said membrane being devoid of apertures therein permitting ingrowth of tissue.

11. A joint prosthesis assembly in accordance with claim 10 wherein the first connector structure comprises a first O-ring fixed to the first end portion of said membrane and engageable with said insert, and a second O-ring fixed to the second end portion of said membrane and engageable with said collar.

12. A joint prosthesis assembly in accordance with claim 10 wherein the first and second end portions are circularly displaced from each other around a central axis therethrough by an angle of about 35°–55°.

13. A joint prosthesis assembly in accordance with claim 10 wherein said middle portion is formed so as to be pre-stressed in a circular direction around a central axis thereof, at an angle of about 35°–55°.

14. A joint prosthesis assembly in accordance with claim 10 wherein said end portions are sufficiently porous to permit the tissue ingrowth, and said middle portion is a selected one of substantially non-porous and insufficiently porous to permit tissue ingrowth.

15. A joint prosthesis assembly in accordance with claim 14 wherein the middle portion is substantially frusto-conically shaped.

16. A joint prosthesis assembly comprising:
   a stem for disposition in a canal of a first bone constituting a first portion of the joint;
   a neck fixed to said stem;
   a collar fixed on said neck;
   an articulating head fixed on said neck;
   a cup for disposition in a second bone constituting a second portion of the joint;
   an insert disposed in said cup to provide an interior lining for said cup, said insert being adapted to receive said articulating head for movement therein; and
   a sleeve-shaped membrane having a first connector structure fixed thereto at a first end thereof for connection to said insert, and a second connector structure fixed thereto at a second end thereof for connection to said collar, said membrane being thereby disposed to capture particulate debris generated by said articulating head in said insert;
   wherein the first and second ends are circularly displaced from each other around a central axis therethrough by an angle of about 35°–55°.

17. A joint prosthesis assembly in accordance with claim 16 wherein the first connector structure comprises a first O-ring fixed to the first end portion of said membrane and engageable with said insert, and a second O-ring fixed to the second end portion of said membrane and engageable with said collar.

18. A joint prosthesis assembly in accordance with claim 16 wherein the first and second end portions of said membrane are provided with apertures therein permitting ingrowth of tissue to further secure said membrane in an operative position, and the middle portion of said membrane is devoid of apertures permitting ingrowth of tissue.

19. A joint prosthesis assembly comprising:
   a stem for disposition in a canal of a first bone constituting a first portion of the joint;
   a neck fixed to said stem;
   a collar fixed on said neck;
   an articulating head fixed on said neck;
   a cup for disposition in a second bone constituting a second portion of the joint;

an insert disposed in said cup to provide an interior lining for said cup, said insert being adapted to receive said articulating head for movement therein; and a sleeve-shaped membrane having a first connector structure fixed thereto at a first end thereof for connection to said insert, and a second connector structure fixed thereto at a second end thereof for connection to said collar, said membrane being thereby disposed to capture particulate debris generated by said articulating head in said insert;

wherein a middle portion of said membrane is formed so as to be pre-stressed in a circular direction around a central axis therethrough, by an angle of about 35°–55°.

20. A joint prosthesis assembly in accordance with claim 19 wherein the first connector structure comprises a first O-ring fixed to the first end portion of said membrane and engageable with said insert, and a second O-ring fixed to the second end portion of said membrane and engageable with said collar.

21. A joint prosthesis assembly in accordance with claim 19 wherein the first and second end portions of said membrane are provided with apertures therein permitting ingrowth of tissue to further secure said membrane in an operative position, and the middle portion of said membrane is devoid of apertures permitting ingrowth of tissue.

22. A method for installing a joint prosthesis assembly, the method comprising the steps of:

providing a joint prosthesis assembly comprising:
a stem for disposition in a canal of a first bone constituting a first portion of the joint;
a neck fixed to said stem;
a collar fixed on said neck, said collar having a peripheral annular groove therein;
an articulating head fixed on said neck;
a cup for disposition in a second bone constituting a second portion of the joint;
an insert disposed in said cup to provide an interior lining for said cup, said insert being adapted to receive said articulating head for movement therein, said insert having a peripheral annular groove therein; and
a sleeve-shaped membrane having a first O-ring fixed thereto at a first end thereof for disposition in the insert groove, and a second O-ring fixed thereto at a second end thereof for disposition in the collar groove;

mounting a first sub-assembly of said stem, neck, collar and articulating head on the first bone, and mounting a second sub-assembly of said cup and insert on the second bone;

mounting the membrane around said articulating head;

fitting said articulating head in said insert; and placing the first O-ring in the insert groove to fix the membrane first end to said insert, and placing the second O-ring in the collar groove to fix the membrane second end to said collar;

said membrane being thereby disposed to capture particulate debris generated by said articulating head in said insert.

23. A method in accordance with claim 22 and including the further step of twisting said membrane circularly about its central axis about 35°–55° before securing the last of (1) the first O-ring to said insert and (2) the second O-ring to said collar, with said membrane in a twisted state.

24. A method in accordance with claim 22 wherein said insert is provided with an annular suture groove proximate but spaced from the insert peripheral annular groove, said membrane is provided with a flexible flap extending from the membrane first end and having a strand of suture connected thereto, and the insert suture groove is adapted to receive the strand of suture, and wherein the first O-ring is provided with tabs extending therefrom, and wherein the steps of placing the first O-ring in the insert groove comprises the steps of:

placing the strand of suture in the insert suture groove;

tightening and tying the strand of suture in the insert suture groove; and manipulating the tabs to pull the first O-ring toward the insert peripheral circular groove until the first O-ring snaps into the insert peripheral annular groove, to fix the membrane first end to the insert.

25. A joint prosthesis assembly in accordance with claim 1 wherein the joint comprises one of the group consisting of a knee joint, a shoulder joint and an elbow joint.

26. A joint prosthesis assembly in accordance with claim 10 wherein said membrane is formed out of PTFE.

27. A joint prosthesis assembly in accordance with claim 26 wherein said first end portion of said membrane and said second end portion of said membrane are formed out of expanded PTFE, and further wherein said middle portion of said membrane is formed out of non-expanded PTFE.

28. A joint prosthesis assembly in accordance with claim 1 wherein said membrane includes an antibiotic.

29. A joint prosthesis assembly in accordance with claim 28 wherein said antibiotic is applied to the surface of said membrane as a coating.

30. A joint prosthesis assembly in accordance with claim 28 wherein said antibiotic is impregnated into the material of said membrane.

* * * * *